(12) United States Patent
Boudry et al.

(10) Patent No.: US 6,277,106 B1
(45) Date of Patent: Aug. 21, 2001

(54) ABSORBENT ARTICLE HAVING AN IMPROVED FASTENABILITY

(75) Inventors: Kristina Michelle Boudry; Chinmay Suresh Betrabet, both of Neenah; Ruth Ann Lachapell, Menasha; Lisha Yu, Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 698 days.

(21) Appl. No.: 08/898,905

(22) Filed: Jul. 23, 1997

Related U.S. Application Data (63) Continuation of application No. 08/559,401, filed on Nov. 15, 1995, now abandoned.

(51) Int. Cl.[7] .................................................. A61F 13/00
(52) U.S. Cl. .............. 604/394; 604/385.01; 604/385.03; 604/386
(58) Field of Search .................. 604/385.1–390, 604/385.01, 385.03, 385.21, 385.22, 385.23, 394, 393, 386

(56) References Cited

U.S. PATENT DOCUMENTS

| | | | |
|---|---|---|---|
| 2,512,713 | * 6/1950 | Cahill | 604/387 |
| 2,649,858 | * 8/1953 | Bott | 604/389 |
| 2,742,903 | * 4/1956 | Lightner | 604/387 |
| 3,906,952 | 9/1975 | Zamist . | |
| 4,061,820 | 12/1977 | Magid et al. . | |
| 4,072,151 | 2/1978 | Levine . | |
| 4,330,888 | 5/1982 | Klepfer . | |
| 4,436,520 | * 3/1984 | Lipko et al. | 604/389 |
| 4,596,244 | * 6/1986 | Jackson | 604/389 |
| 4,743,242 | * 5/1988 | Grube et al. | 604/389 |
| 4,753,648 | 6/1988 | Jackson | 604/389 |
| 4,798,603 | 1/1989 | Meyer et al. | 604/378 |
| 4,850,992 | * 7/1989 | Amaral et al. | 604/389 |
| 5,066,289 | * 11/1991 | Polski | 604/389 |
| 5,071,415 | * 12/1991 | Takemoto | 604/389 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. | 428/284 |
| 5,342,339 | * 8/1994 | Carpenter et al. | 604/385.1 |
| 5,445,627 | * 8/1995 | Mizutani et al. | 604/389 |
| 5,510,161 | * 4/1996 | Loyd | 604/390 |
| 5,616,385 | * 4/1997 | Rothrum et al. | 604/390 |
| 5,660,659 | * 8/1997 | Caldwell | 604/390 |

FOREIGN PATENT DOCUMENTS

| | | |
|---|---|---|
| 0 528 282 A3 | 2/1993 | (EP) . |
| 2 284 767 A | 6/1995 | (GB) . |
| H6-9622 | 2/1994 | (JP) . |

* cited by examiner

*Primary Examiner*—John G. Weiss
(74) *Attorney, Agent, or Firm*—Jeffrey B. Curtin; Alyssa A. Dudkowski (57) ABSTRACT

The present invention provides a diaper which includes an outer cover, a bodyside liner which is superposed on the outer cover and which includes a bodyfacing surface, an absorbent core which is located between the outer cover and the bodyside liner, and an adhesive. The adhesive is located on the bodyfacing surface of the bodyside liner. The adhesive is configured to at least temporarily secure the front portion of the diaper to a wearer's body to assist in positioning and fastening the diaper about the wearer's body. In a particular aspect, the adhesive is configured to provide a peel strength of no more than about 300 grams per centimeter of width and an initial shear strength of no more than about 600 grams per square centimeter.

31 Claims, 6 Drawing Sheets

ABSORBENT ARTICLE HAVING AN IMPROVED FASTENABILITY

This application is a continuation of application Ser. No. 08/559,401 entitled "ABSORBENT ARTICLE HAVING AN IMPROVED FASTENABILITY" and filed in the U.S. Patent and Trademark Office on Nov. 15, 1995 and now abandoned.

BACKGROUND OF THE INVENTION

The present invention relates to a disposable absorbent article having an improved fastenability about the waist of a wearer. In particular, the present invention relates to a disposable diaper which includes an adhesive to assist the care-giver in positioning and fastening the diaper about the waist of the wearer.

Disposable absorbent articles such as diapers, incontinence articles, training pants and the like are well known to those skilled in the art. Such absorbent articles generally include a front portion, a rear portion and a crotch portion connecting the front portion to the rear portion. As used herein, reference to a front portion refers to that part of the absorbent article which is generally located on the front of a wearer when in use. Reference to the rear portion refers to the portion of the absorbent article generally located at the rear of the wearer when in use, and reference to the crotch portion refers to that portion which is generally located between the legs of the wearer when in use.

Many of the conventional absorbent articles, and diapers in particular, are typically fastened about the waist of the wearer using fasteners which can be releasably engaged together. The fasteners generally include a pair of first fasteners which are located on the side edges of the rear portion of the absorbent article and at least one second fastener which is located on the front portion of the absorbent article. In use, the first fasteners are configured to be releasably engageable with the second fastener to fasten the absorbent article about the waist of the wearer.

The process used to fasten such conventional absorbent articles about a wearer typically includes the following steps: (1) placing the absorbent article in a laid out flat configuration; (2) positioning the back torso of the wearer on the rear portion of the absorbent article; (3) bringing the front portion of the absorbent article between the legs of the wearer; (4) extending the fasteners about the side regions of the waist of the wearer; and (5) releasably engaging the fasteners together to secure the absorbent article about the waist of the wearer. Such an involved process can be extremely difficult for a care-giver to accomplish. For example, after bringing the front portion of the absorbent article between the legs of the wearer, the care-giver typically uses one hand to hold the front portion of the absorbent article against the stomach of the wearer, while the other hand releasably engages the fasteners about one side of the wearer. The care-giver must then switch hands and complete the same procedure on the opposite side of the wearer. In such a process, it can be very difficult for the care-giver to maintain the absorbent article in a proper position while releasably engaging the fasteners together along both side edges of the waist of the wearer. This is particularly true when the wearer is very active.

As a result, the conventional absorbent articles and the process of fastening such articles about the waist of a wearer have not been completely satisfactory. The design of the conventional absorbent articles and the complex process required in using them can easily frustrate the care-giver or person fastening the article about the wearer. Moreover, the conventional article design and fastening process can result in an improper positioning of the absorbent article about the wearer. Such improper positioning can result in an undesirable increase in leakage of body exudates from the absorbent article and decreased consumer acceptance. Typically, when using the conventional absorbent articles, the care-giver may be required to readjust or reposition the absorbent article two or more times to achieve the optimum placement and fit of the article about the wearer.

Many conventional absorbent articles have included fasteners which are attached to tabs of material or ears which extend beyond the side edges of the absorbent article to improve the fastenability of the absorbent article about the waist of the wearer. However, although such improvements have increased the ease of fastening, it remains desirable to provide an absorbent article which has an improved fastenability about the waist of the wearer. In particular, it is desirable to provide an absorbent article having improved fastening ergonomics which can result in an improved fit and positioning of the absorbent article about the wearer upon an initial fastening to provide improved performance.

Moreover, conventional absorbent articles which have utilized leg and waist gathers have still had a tendency to leak body exudates at the leg and waist regions. Further, the waist regions on conventional absorbent articles have also undesirably rolled over or sagged and drooped after a period of usage. Accordingly, it is also desirable to provide an absorbent article which has reduced leakage and which has waist regions which have a reduced tendency to roll over or droop.

SUMMARY OF THE INVENTION

In response to the discussed difficulties and problems, a new disposable absorbent article having an improved fastenability about a wearer has been discovered.

In one aspect, the present invention concerns an absorbent article which includes a front portion, a rear portion, a crotch portion which extends between and connects the front portion to the rear portion, a pair of side edges and a pair of longitudinal end edges. The absorbent article also includes an outer cover, a bodyside liner which is superposed on the outer cover and which includes a bodyfacing surface and an absorbent core which is located between the outer cover and the bodyside liner. The absorbent article further includes an adhesive which is located on the bodyfacing surface of the bodyside liner. The adhesive is configured to provide a peel strength of no more than about 300 grams per centimeter of width of the adhesive pattern.

In another aspect, the present invention concerns an absorbent article which includes an adhesive which is located on the bodyfacing surface of the bodyside liner and which is configured to at least temporarily secure the absorbent article to a wearer's body. The adhesive is configured to provide a peel strength of no more than about 300 grams per centimeter of width, an aged shear strength of no more than about 500 grams per square centimeter and a cyclic shear value of no more than about 100 cycles. In a particular aspect, the adhesive is located on the bodyfacing surface of the bodyside liner in the front portion of the absorbent article. In such a configuration, the adhesive is configured to at least temporarily secure the front portion of the absorbent article to the wearer's body to assist in positioning and fastening the absorbent article about the wearer's body.

In yet another aspect, the present invention concerns a diaper which includes a front portion, a rear portion, a crotch portion which extends between and connects the front portion to the rear portion, a pair of side edges and a pair of longitudinal end edges. The diaper also includes an outer cover, a bodyside liner which is superposed on the outer cover and which includes a bodyfacing surface, an absorbent core which is located between the outer cover and the bodyside liner, and an adhesive. The adhesive is located on the bodyfacing surface of the bodyside liner adjacent at least a portion of the longitudinal end edge of the diaper in the front portion of the diaper. The adhesive is configured to at least temporarily secure the front portion of the diaper to a wearer's body to assist in positioning and fastening the diaper about the wearer's body. In a particular aspect, the adhesive is configured to provide a peel strength of no more than about 300 grams per centimeter of width and an initial shear strength of no more than about 600 grams per square centimeter.

The present invention can advantageously provide an absorbent article which has improved fastenability. The absorbent article according to the different aspects of the present invention has improved fastening ergonomics to allow the care-giver to properly position and fasten the absorbent article about the waist of a wearer on the first try. As such, the present invention can provide an absorbent article which has reduced leakage because it is easier to position on the wearer to obtain the optimum fit.

Moreover, the present invention can advantageously provide an absorbent article which has improved seals at the leg and waist regions to reduce the leakage of bodily exudates. The present invention can also provide an absorbent article which has waist regions which have a reduced tendency to rollover or droop and sag. Accordingly, the present invention can provide an absorbent article which is easier to fasten about the wearer and has an improved fit, reduced leakage and increased consumer acceptance.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the claims.

DETAILED DESCRIPTION OF THE INVENTION

The present invention relates to a disposable absorbent article having an improved fastenability about the waist of a wearer. The term "disposable absorbent article" is intended to refer to any disposable article intended to be worn and attached to a wearer to absorb discharged body fluids. Examples of disposable absorbent articles include diapers, adult incontinence products, training pants, feminine care products, and the like. For ease of understanding, much of the following description of the present invention will be made in terms of disposable diapers. Nonetheless, it is to be understood that the present invention is equally suited for use as any other disposable absorbent article.

FIGS. 1–6 representatively illustrate different diaper configurations according to the present invention wherein like numerals represent like elements. As representatively illustrated in FIGS. 1–6, the diaper 20 defines a front portion 22, a rear portion 24, a crotch portion 26 connecting the front portion 22 and the rear portion 24, a pair of opposite side edges 28 and a pair of opposite longitudinal end edges 30. The diaper 20 includes an outer cover 32, a bodyside liner 34 and an absorbent core 38 located between the bodyside liner 34 and the outer cover 32. The bodyside liner 34 includes a bodyfacing surface 36 which is intended to provide a contacting relationship with a wearer's body in use. The diaper 20 also includes an adhesive 50 located on the bodyfacing surface 36 of the bodyside liner 34.

The opposite side edges 28 of the diaper 20 may include a pair of elasticized, longitudinally-extending leg cuffs 42. The leg cuffs 42 are generally adapted to fit about the legs of the wearer in use and serve as a mechanical barrier to the lateral flow of body exudates. The diaper 20 may also include a front and rear waist elastic 44 to help reduce leakage at the front and back waist of the wearer when in use. The leg cuffs 42 and waist elastics 44 may be elasticized by elastic members as are well known to those skilled in the art. The diaper 20 may further include a pair of fasteners 46 which are intended to hold the diaper 20 about the waist of the wearer when in use. Suitable fasteners 46 include adhesive tape fasteners, hook-and-loop type fasteners, buttons, snaps and the like as are also well known to those skilled in the art. The diaper 20 may also include a pair of elasticized, longitudinally-extending containment flaps 48 which are configured to maintain an upright, perpendicular arrangement in at least the crotch portion 26 of the diaper 20 to serve as an additional barrier to the lateral flow of body exudates.

The outer cover 32 of the diaper 20, as representatively illustrated in FIGS. 1–6, may suitably be composed of a material which is either liquid permeable or liquid impermeable. It is generally preferred that the outer cover 32 be formed from a material which is substantially impermeable to liquids. For example, a typical outer cover can be manufactured from a thin plastic film or other flexible liquid-impermeable material. For example, the outer cover 32 may be formed from a polyethylene film having a thickness of from about 0.013 millimeter (0.5 mil) to about 0.051 millimeter (2.0 mils). If it is desired to present the outer cover 32 with a more clothlike feeling, the outer cover 32 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 32 may be formed of a woven or nonwoven fibrous web layer which has been totally or partially constructed or treated to impart a desired level of liquid impermeability to selected regions that are adjacent or proximate the absorbent core 38. Still further, the outer cover 32 may optionally be composed of a micro-porous "breathable" material which permits vapors to escape from the absorbent core 38 while still preventing liquid exudates from passing through the outer cover 32.

The bodyside liner 34 of the diaper 20, as representatively illustrated in FIGS. 1–6, suitably presents a bodyfacing surface 36 which is compliant, soft feeling, and nonirritating to the wearer's skin. Further, the bodyside liner 34 may be less hydrophilic than the absorbent core 38, to present a relatively dry surface to the wearer, and may be sufficiently porous to be liquid permeable, permitting liquid to readily penetrate through its thickness. A suitable bodyside liner 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 34 is suitably employed to help isolate the wearer's skin from liquids held in the absorbent core 38.

Various woven and nonwoven fabrics can be used for the bodyside liner 34. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 34 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation Triton X-102.

The absorbent core 38 of the diaper 20, as representatively illustrated in FIGS. 1–6, may suitably comprise a matrix of hydrophilic fibers, such as a web of cellulosic fluff, mixed with particles of a high-absorbency material commonly known as superabsorbent material. In a particular embodiment, the absorbent core 38 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed, Alternatively, the absorbent core 38 may comprise a laminate of fibrous webs and superabsorbent material or other suitable means of maintaining a superabsorbent material in a localized area.

The absorbent core 38 may have any of a number of shapes. For example, the absorbent core may be rectangular, I-shaped, or T-shaped. It is generally preferred that the absorbent core 38 be narrower in the crotch portion 26 than in the front or rear portions 22 and 24 of the diaper 20, respectively.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively-rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent core in an amount of from about 5 to about 90 weight percent based on total weight of the absorbent core 38.

The outer cover 32 and bodyside liner 34 are generally adhered to one another so as to form a pocket in which the absorbent core 38 is located. Thus, the side edges 28 and longitudinal end edges 30 of the disposable diaper 20 are suitably formed by portions of the outer cover 32, and/or bodyside liner 34, which extend beyond the sides and longitudinal ends of the absorbent core 38. The leg cuffs 42 are suitably formed from the side edges 28 but may also be formed from separate materials which are attached to the outer cover 32 and/or bodyside liner 34. The different components of the disposable diaper 20 may be bonded together by any means known to those skilled in the art such as adhesive bonding, ultrasonic bonding, thermal bonding and the like.

The leg cuffs 42, as representatively illustrated in FIGS. 1–6, may include leg elastics as are known to those skilled in the art. Suitable materials which can be used for the leg elastics are strands or ribbons of a polymeric, elastomeric material which are adhered to the diaper 20 at the leg cuffs 42 while in a stretched position, or which are attached to the diaper while the diaper is pleated, such that elastic constrictive forces are imparted to the leg cuffs 42. The leg cuffs 42 may be elasticized along any portion of their length which provides the desired seal against the legs of the wearer. Waist elastics 44 and containment flaps 48, as representatively illustrated in FIGS. 1–6, may also be elasticized and are well known to those skilled in the art. One skilled in the art will recognize that the diaper 20 according to the different aspects of the present invention may omit one or more of the described components, such as the waist elastics 44 or containment flaps 48, depending upon the desired diaper design.

Specific examples of disposable diapers on which the adhesive of the present invention may be utilized are disclosed in the following U.S. Patents and U.S. patent applications: U.S. Pat. No. 4 798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; and U.S. patent application Ser. No. 08/096,654 filed Jul. 22, 1993, in the name of Hanson et al.

As representatively illustrated in FIGS. 1–6, the diaper 20 of the present invention further includes an adhesive 50 which is located on the bodyfacing surface 36 of the bodyside liner 34 and arranged in an adhesive pattern. The adhesive 50 is configured to at least temporarily adhere to the body of the wearer. Suitable adhesives for use in the present invention are those that exhibit the desired level of adhesion to the skin for the particular application but which releases from or can be removed from the wearer with a minimum level of discomfort. It is generally preferred that the adhesive 50 adheres to the skin of the wearer without noticeable redmarking after it releases or has been removed.

The adhesive 50 of the diaper 20, as representatively illustrated in FIGS. 1–6, is configured to at least temporarily contact and adhere to the wearer's body to assist in positioning and fastening the diaper 20 about the waist of the wearer. In such a configuration, the adhesive 50 may temporarily secure the diaper 20 on the wearer's body for a sufficient amount of time such that the care-giver can releasably engage the fasteners 46 to maintain the diaper 20 about the wearer's body. After the diaper 20 is fastened about the wearer, the adhesive may release from the skin of the wearer or may remain adhered to the wearer for an extended duration especially if the wearer continues to exert a force pressing the adhesive onto the skin. The adhesive 50 can be located in any pattern on any location on the bodyfacing surface 36 of the bodyside liner 34 which provides the desired temporary securement and fastening improvement.

Figure 1:
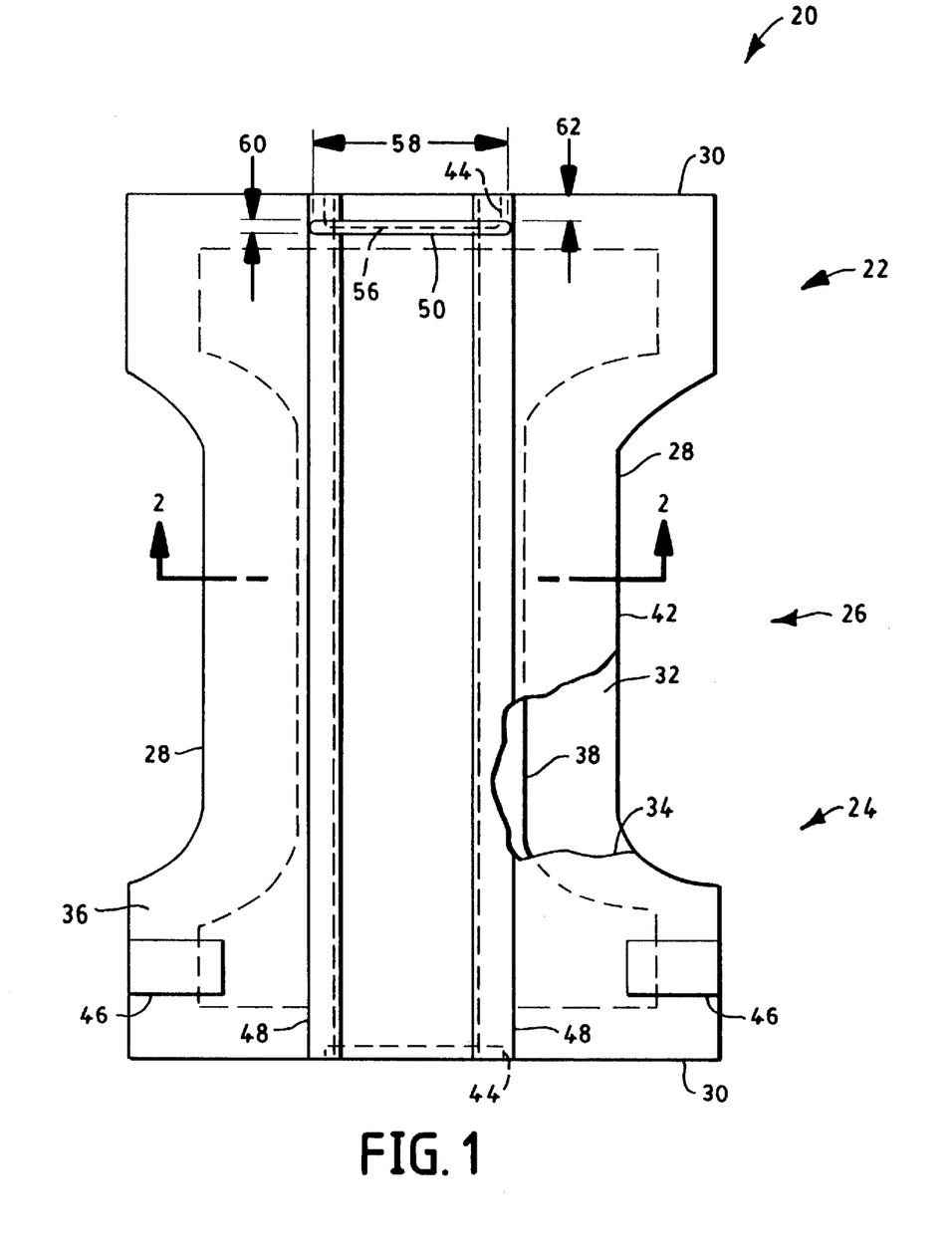
FIG. 1 representatively illustrates a top plan view of an example of a disposable diaper according to the present invention.
Figure 2:
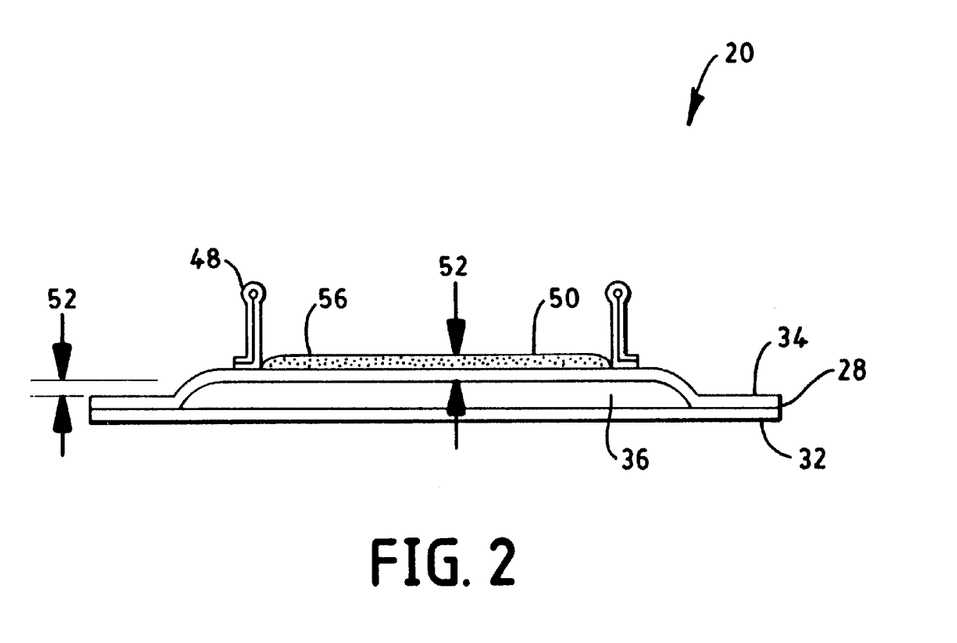
FIG. 2 is a cross-sectional view of the disposable diaper representatively illustrated in FIG. 1 taken along line 2—2.
Figure 3:
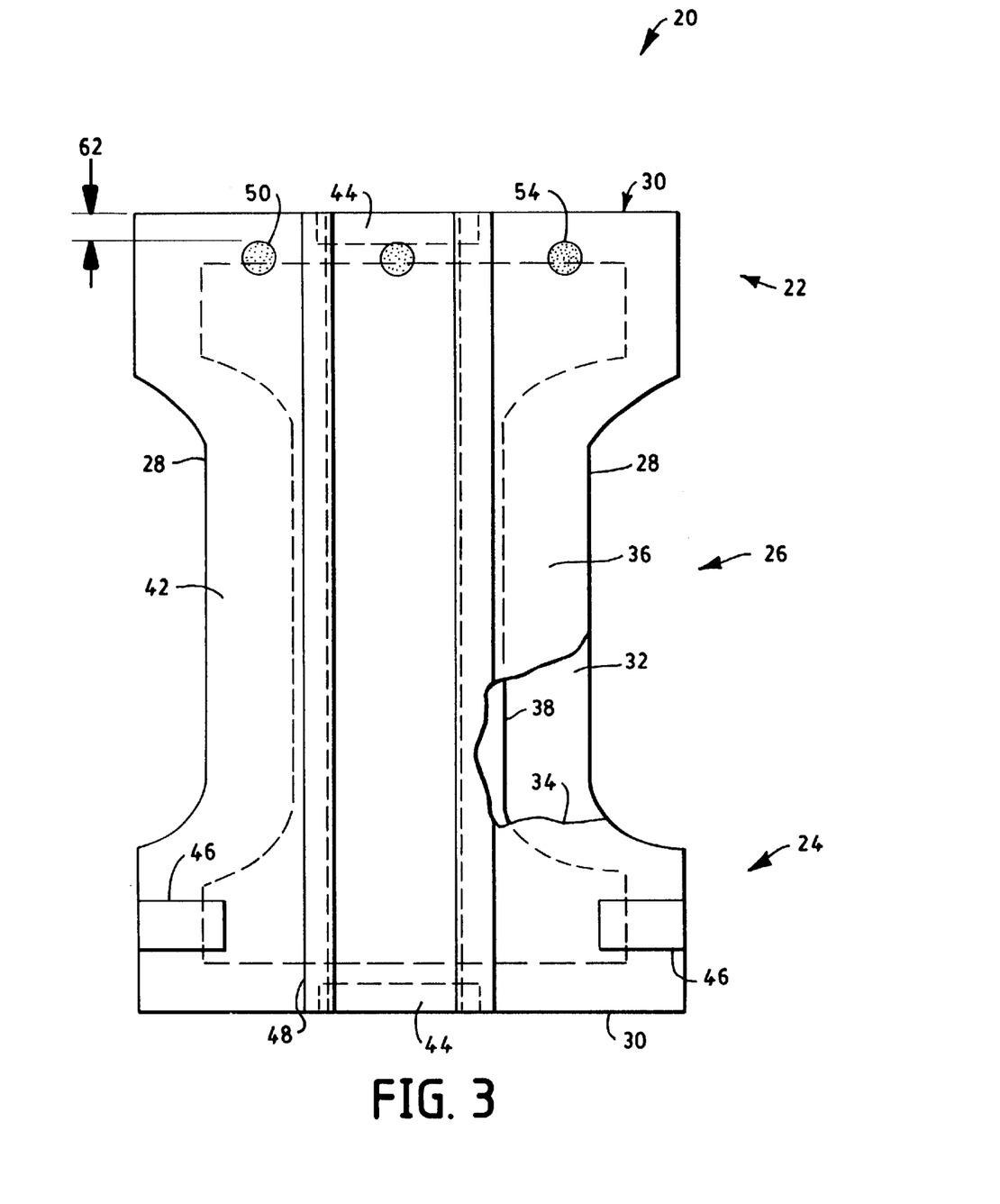
FIG. 3 representatively illustrates a top plan view of another example of a disposable diaper according to the present invention.

For example, in one configuration, as representatively illustrated in FIGS. 1–3, the adhesive 50 can be located on the bodyfacing surface 36 of the bodyside liner 34 in the front portion 22 of the diaper 20. In use, the diaper 20 may then be secured about the wearer according to the following steps: (1) placing the diaper 20 in a laid out flat configuration with the bodyfacing surface 36 of the bodyside liner 34 exposed; (2) positioning the back torso of the wearer on the bodyside liner 34 in the rear portion 24 of the diaper 20; (3) bringing the front portion 22 of the diaper between the legs of the wearer; (4) applying pressure to press the adhesive 50 against the wearer's body to temporarily secure at least the front portion 22 of the diaper 20 to the wearer's body; (5) extending the fasteners 46 about the side regions of the waist of the wearer; and (6) releasably engaging the fasteners 46 with the front portions 22 of the diaper 20 to secure the diaper 20 about the waist of the wearer.

Accordingly, in such a configuration, the adhesive 50 allows the care-giver to use both hands to releasably engage both fasteners 46 simultaneously to secure the diaper 20 about the wearer's body in the optimum location on the first try. As a result, the use of the adhesive 50 can provide a diaper 20 which has an improved fastenability about a wearer. This is particularly true when the wearer is active. Thus, in one aspect, the present invention provides a diaper 20 which can be positioned on the wearer in the optimum location for improved performance with minimal effort.

Several factors affect the ability of the adhesive to achieve the desired temporary securement of the absorbent article about the wearer to assist the care-giver in positioning and attaching the diaper about the wearer. These factors may include the type of adhesive, the rheological properties of the adhesive such as, for example, the shear storage modulus and tan delta of the adhesive, the peel strength of the adhesive, the shear strength of the adhesive, the amount of adhesive, the pattern of adhesive, the force used to initially secure the adhesive to the body of the wearer, and any external forces acting on the adhesive such as the weight of the diaper 20 and the level of activity of the wearer.

Any adhesives which provide the desired temporary securement of the diaper 20 to the wearer without discomfort to the wearer can be used in the present invention. Suitable adhesives may include hydrogels, silicones, acrylics, polyurethanes, polyesters, and polyamides. Other suitable adhesives include a rubber-based adhesive such as styrenebutadiene, polyisobutylene, polybutadiene and polyisoprene; a water soluble adhesive such as polyvinyl alcohol, polyvinyl acetate and methyl cellulose; and, desirably, a hot melt adhesive such as block copolymers of styrene-butadiene-styrene, styrene-isoprene-styrene, styrene-ethylenepropylene-styrene, styrene-ethylenebutylene-styrene and tetrablock copolymers such as styrene-ethylenepropylene-styrene-ethylenepropylene. Desirably, the adhesive 50 is a pressure sensitive adhesive. The adhesive 50 may also include other substances such as tackifying resins, oils and the like. Such adhesives are commercially available from Findley Adhesives Company, a business having offices in Wauwatosa, Wisconsin and the National Starch and Chemical Company, a business having offices located in Bridgewater, New Jersey.

When the adhesive 50 of the present invention is used primarily to provide a diaper 20 which has improved fastenability about the wearer, it is desirable that the adhesive 50 have a low adhesion to the skin such that it releases from the skin after a relatively short period of time. It has been discovered that suitable adhesives to provide such an improved fastenability are those which have the following properties.

As used herein, the term "shear storage modulus" refers to the shear storage modulus value determined according to the methods described in the Test Methods section below. The shear storage modulus value of an adhesive is meant to represent the flexibility or stretchability of the adhesive. In the different aspects of the present invention, it is desired that the adhesive 50 does not exhibit a shear storage modulus which is too low, since such will generally indicate that the adhesive lacks sufficient cohesive strength and will,.thus, generally break apart and leave residue upon removal from a wearer's skin. Generally, adhesives which exhibit a higher shear storage modulus are desirable when the adhesive 50 is configured to release from the skin after a short period of time. However, as the shear storage modulus of the adhesive increases, the flexibility of the adhesive will decline. Thus, an adhesive which exhibits a shear storage modulus which is too high may not conform to the wearer's body or may cause mechanical irritation.

Thus, to achieve a generally low level of adhesion to the wearer to provide the desired temporary securement, the adhesive 50 of the present invention exhibits a shear storage modulus of at least about $1.0 \times 10^3$ and desirably at least about $7.8 \times 10^3$ dynes per square centimeter as measured at a temperature of about 20° C. and at a frequency of about 10 radians per second. For example, the adhesive may exhibit a shear storage modulus of from about $1.0 \times 10^3$ to about $6.0 \times 10^5$ and desirably from about $4.0 \times 10^4$ to about $6.0 \times 10^6$ dynes per square centimeter as measured at a temperature of about 20° C. and at a frequency of about 10 radians per second.

As used herein, the term "tan delta" refers to the tan delta value determined according to the methods described in the Test Methods section below. The tan delta value of an adhesive is meant to represent the ratio between the shear loss modulus and the shear storage modulus of the adhesive.

As used herein, the term "peel strength" refers to the peel strength of the adhesive as determined according to the Peel Strength Test described in the Test Methods section below. The peel strength of an adhesive is meant to represent the adhesive bond strength of the adhesive. In the different aspects of the present invention, it is desired that the adhesive 50 does not exhibit a peel strength which is too high, since such will generally indicate that the adhesive is too aggressive and will, thus, remain adhered to the skin of the wearer and cause pain and redmarking upon removal from the skin. Generally, adhesives which exhibit a lower peel strength are desirable when the adhesive 50 is configured to release from the skin after a short period of time. However, as the peel strength of the adhesive decreases, the adhesive may not adhere at all to the wearer's body.

Thus, to achieve the desired level of adhesion to the wearer to provide the desired temporary securement, the adhesive 50 of the present invention exhibits a peel strength of no more than about 300 grams per centimeter of width, desirably no more than about 240 grams per centimeter of width, and more desirably no more than about 160 grams per centimeter of width of the adhesive pattern. For example, the adhesive 50 may exhibit a peel strength of from about 0 to about 240 grams per centimeter of width, desirably from about 10 to about 160 grams per centimeter of width, and more desirably from about 40 to about 100 grams per centimeter of width of the adhesive pattern.

The shear strength of an adhesive is another property of adhesives which is important to the selection of an appropriate adhesive for use in the present invention. The shear strength of an adhesive may vary as the duration of use extends. Accordingly, the shear strength of an adhesive can be determined at the time of application to provide an initial shear strength and at any later designated time to provide an aged shear strength. As used herein, the terms "initial shear strength" and "aged shear strength" refer to the shear strength of the adhesive as determined according to the Shear Strength Test described in the Test Methods section below.

The shear strength of an adhesive is also meant to represent the adhesive bond strength of the adhesive. In the different aspects of the present invention, it is desired that the adhesive 50 does not exhibit an initial shear strength which is too high, since such will generally indicate that the adhesive is too aggressive and will, thus, remain adhered to the skin of the wearer and cause pain and redmarking upon removal from the skin. Generally, adhesives which exhibit a lower initial shear strength are desirable when the adhesive 50 is configured to release from the skin after a short period of time.

Thus, to achieve the desired level of adhesion to the wearer, the adhesive 50 of the present invention exhibits an initial shear strength of no more than about 600 grams per square centimeter, desirably no more than about 530 grams per square centimeter, and more desirably no more than about 430 grams per square centimeter of the adhesive pattern. For example, the adhesive 50 may exhibit an initial shear strength of from about 0 to about 530 grams per square centimeter and desirably from about 30 to about 430 grams per square centimeter of the adhesive pattern.

The aged shear strength of an adhesive is meant to represent the shear strength of the adhesive after a specific period of time. Thus, the aged shear strength can indicate the likelihood of the adhesive to release from the skin after a short period of time. In the different aspects of the present invention, it is desired that the adhesive 50 does not exhibit an aged shear strength which is too high, since such will generally indicate that the adhesive is too aggressive and will, thus, remain adhered to the skin of the wearer and cause pain and redmarking upon removal from the skin. Generally, adhesives which exhibit a lower aged shear strength are desirable when the adhesive 50 is configured to release from the skin after a short period of time.

Thus, to achieve the desired level of adhesion to the wearer to provide the desired temporary securement of the diaper 20 about the wearer, the adhesive 50 of the present invention exhibits an aged shear strength of no more than about 500 grams per square centimeter, desirably no more than about 450 grams per square centimeter, and more desirably no more than about 400 grams per square centimeter of the adhesive pattern. For example, the adhesive 50 may exhibit an aged shear strength of from about 0 to about 400 grams per square centimeter, desirably from about 20 to about 340 grams per square centimeter, and more desirably from about 30 to about 250 grams per square centimeter of the adhesive pattern.

As described above, it is desirable that the adhesive of the different aspects of the present invention releases from the skin of the wearer after a period of time. Another property of an adhesive, the cyclic shear, can be used in the selection of an appropriate adhesive for use in the present invention. As used herein, the term "cyclic shear" refers to the cyclic shear value of the adhesive as determined according to the Cyclic Shear Test described in the Test Methods section below.

In general, the cyclic shear of an adhesive represents the decreasing ability of an adhesive to remain adhered to the skin of a wearer as the wearer moves during use. The cyclic shear is a measure of the number of cycles of movement which an adhesive can endure before separating from a surface. In the different aspects of the present invention, it is desired that the adhesive 50 does not exhibit a cyclic shear which is too high, since such will generally indicate that the adhesive is too aggressive or too compliant and stretchable and will, thus, remain adhered to the skin of the wearer. Generally, adhesives which have a low cyclic shear, detach from the skin of the wearer after a relatively short duration.

Thus, the adhesive 50 of the present invention exhibits a cyclic shear of no more than about 100 cycles and desirably no more than about 50 cycles as tested according to the Cyclic Shear Test. For example, the adhesive 50 may exhibit a cyclic shear of from 0 to about 100 cycles, desirably from 0 to about 50 cycles, and more desirably from 0 to about 20 cycles.

In a particular aspect, the adhesive of the present invention exhibits a peel strength of no more than about 300 grams per centimeter of width, an initial shear strength of no more than about 600 grams per square centimeter, and a cyclic shear value of no more than about 100 cycles for improved performance.

To provide the improved fastenability and at least temporary securement of the diaper 20 to the wearer's body, the adhesive 50 need not cover the entire surface area of the bodyfacing surface 36 of the bodyside liner 34. For example, the adhesive 50 may be located on no more than about 75 percent, desirably no more than about 25 percent and more desirably no more than about 10 percent of the surface area of the bodyfacing surface 36 of the bodyside liner 34. The amount of adhesive 50 will depend upon the size and weight of the diaper 20, the type of adhesive, the pattern of the adhesive, and the desired level and duration of adhesion to the wearer. The adhesive 50 may have an adhesive surface area which is at least about 0.5 square centimeters, desirably from about 0.1 to about 10 square centimeters and more desirably from about 0.5 to about 4 square centimeters to provide sufficient temporary securement of the diaper 20 to the wearer. The adhesive 50 is desirably applied to the desired portions of the bodyside liner 34 at in add-on level of from about 0.001 grams per square centimeter to about 0.50 grams per square centimeter for improved performance.

The adhesive 50 can be arranged in any pattern or configuration which provides the improved fastenability of the diaper 20 about the waist of the wearer. Suitable patterns include single or multiple strips of adhesive, an array of dots or ovals of adhesive, swirls of adhesive, linear and non-linear arrays of adhesive, reticulated patterns of adhesive fibers and the like. For example, in one configuration as representatively illustrated in FIGS. 1 and 2, the adhesive 50 may include a single strip of adhesive 56 which extends laterally along the longitudinal end edge 30 of the diaper 20. Desirably, the single strip of adhesive 56 is located in the front portion 22 of the diaper 20.

The strip of adhesive 56, as representatively illustrated in FIGS. 1 and 2, may have a length 58 of from about 1 to about 35 centimeters and desirably from about 2 to about 8 centimeters to provide the at least temporary securement and improved fastenability. The strip of adhesive 56 may also have a width 60 of from about 0.5 to about 5 centimeters and desirably from about 0.5 to about 2 centimeters and a thickness 52 of from about 0.001 to about 1 millimeter. The strip of adhesive 56 may also be spaced inwardly from the longitudinal end edge 30 of the diaper 20 a distance of from about 0 to about 6 centimeters and desirably from about 0 to about 2.5 centimeters to provide improved performance.

As representatively illustrated in FIG. 3, the adhesive 50 may also be arranged as a pattern of dots 54 selectively located on the bodyfacing surface 36 of the bodyside liner 34 of the diaper 20 in the front portion 22 of the diaper 20 to provide the desired improved fastenability. For example, from 1 to about 15 dots of adhesive may be located in the front portion 22 of the diaper 20. The dots 54 may be arranged in any suitable configuration which may be linear or non-linear. To provide the desired amount of adhesive surface area, each dot 54 may have a surface area of from about 0.04 to about 9.0 square centimeters and desirably from about 0.36 to about 3.0 square centimeters.

The low levels of adhesion and short duration of adhesion to the skin of the wearer of the adhesive 50 of the present invention advantageously provide sufficient temporary securement of the diaper 20 to the wearer to improve the fastenability of the diaper 20 while maintaining the level of irritation, red marking and discomfort to the wearer at a minimum. Such adhesives, having the properties described above, are capable of providing at least sufficient temporary adhesion to the body of the wearer to allow the care-giver enough time to fasten the diaper 20 about the waist of the wearer using both hands. A particularly suitable adhesive 50 for use in providing the at least temporary securement and improved fastenability is an adhesive which is based on polyisobutylene and is formulated from three components. Two components are commercially available from Exxon Chemical Company, a business having offices located in Baytown, Tex., under the trade designation Vistanex L-120 and Butyl 065. The third component is commercially available from Amoco Chemical Company, a business having offices located in Chicago, Ill., under the trade designation Polybutene H-25. The components are mixed according to the procedure set forth in Example 8.

The adhesive 50 of the present invention may also be configured to provide other benefits. For example, as representatively illustrated in FIGS. 1–6, the adhesive 50 may be located in the front portion 22 of the diaper 20 to reduce the rollover of the end edge 30 of the front portion 22 of the diaper 20. The reduction in rollover of the front edge of the diaper may result in reduced leakage of body exudates.

The adhesive 50 of the different aspects of the present invention may also be configured to provide additional support for the diaper 20 about the wearer to maintain the diaper 20 in a proper position on the body of the wearer when in use to ensure an optimum fit to reduce leakage. For example as representatively illustrated in FIGS. 4–6, the adhesive 50 may be selectively located about the outer periphery of the diaper 20 to help support the diaper 20 about the wearer to minimize any sagging or drooping of the diaper 20. The adhesive 50 may also be configured to maintain selected regions or components of the diaper 20 in a contacting relationship with the body of the wearer when in use. For example, the adhesive 50 may be located in the crotch portion 26 of the diaper 20 to maintain the crotch portion 26 in a contacting relationship with the wearer.

Further, the adhesive 50 may be selectively located on the bodyfacing surface 36 of the bodyside liner 34 of the diaper 20 to also provide a seal or barrier around at least a portion of the outer perimeter of the diaper 20. For example, as representatively illustrated in FIGS. 4 and 5, the diaper 20 may include a pair of strips of adhesive 56 which extend laterally along each longitudinal end edge 30 of the diaper 20 to reduce the leakage of body exudates along the front and back waist of the wearer. Such a configuration is particularly effective in reducing leakage in diapers which are intended for use by male infants. The strips of adhesive 56 may have a length 58 of from about 1 to about 35 centimeters and desirably from about 5 to about 10 centimeters to provide the desired seal and barrier. The strips of adhesive 56 may also have a width 60 of from about 0.5 to about 5 centimeters and desirably from about 0.5 to about 2 centimeters and a thickness 52 of from about 0.001 to about 5 millimeters to help reduce the leakage of body exudates. Further, the strips of adhesive 56 may be spaced inwardly from the longitudinal end edge 30 of the diaper 20 a distance of from about 0 to about 6 centimeters and desirably from about 0 to about 2.5 centimeters to provide improved performance.

Figure 4:
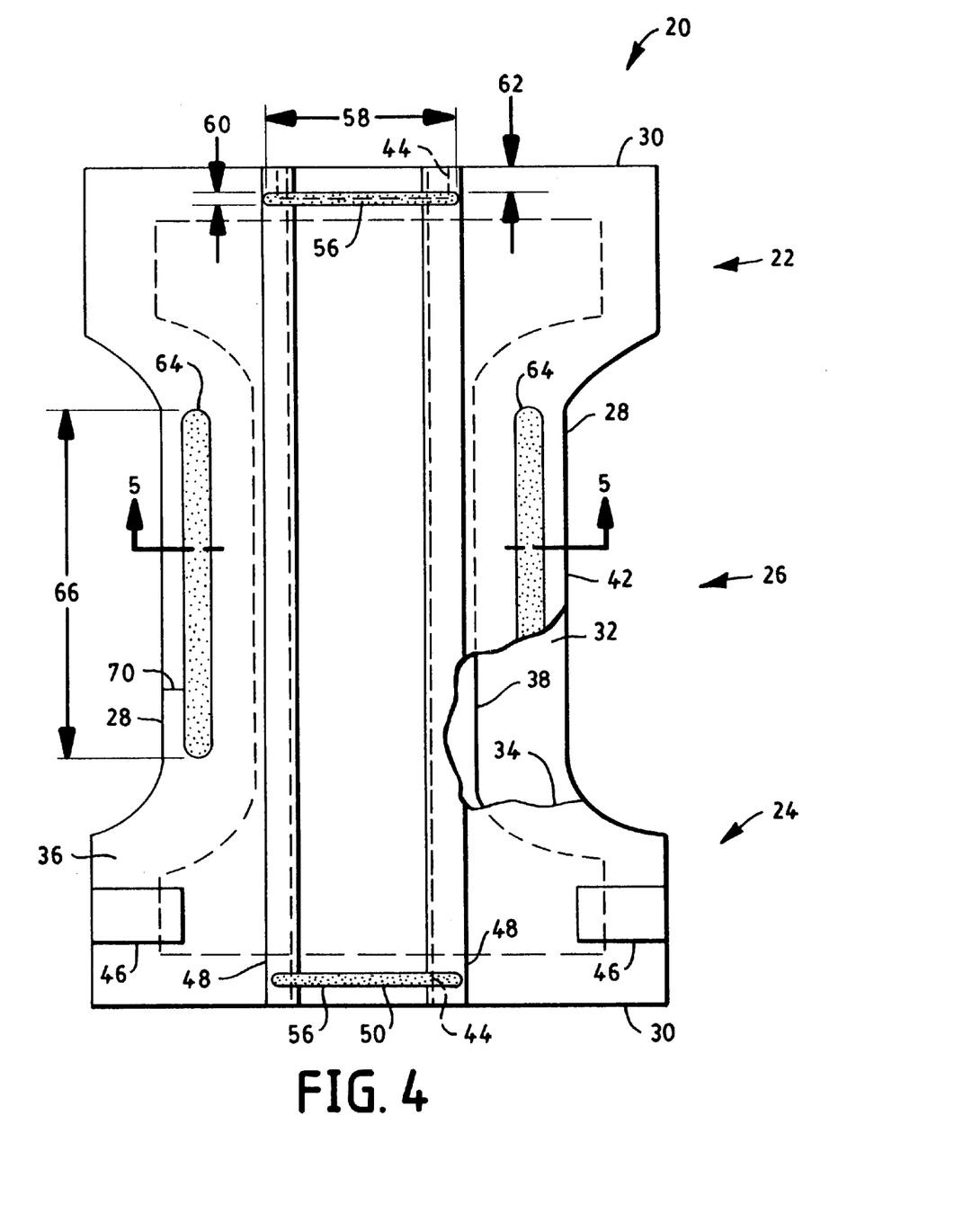
FIG. 4 representatively illustrates a top plan view of a further example of a disposable diaper according to the present invention.
Figure 5:
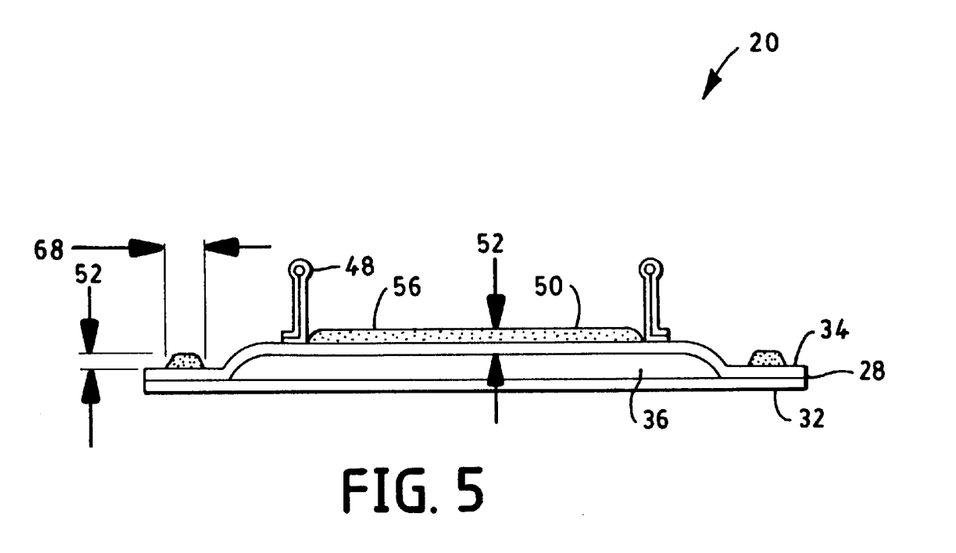
FIG. 5 is a cross-sectional view of the disposable diaper representatively illustrated in FIG. 4 taken along line 5—5.
Figure 6:
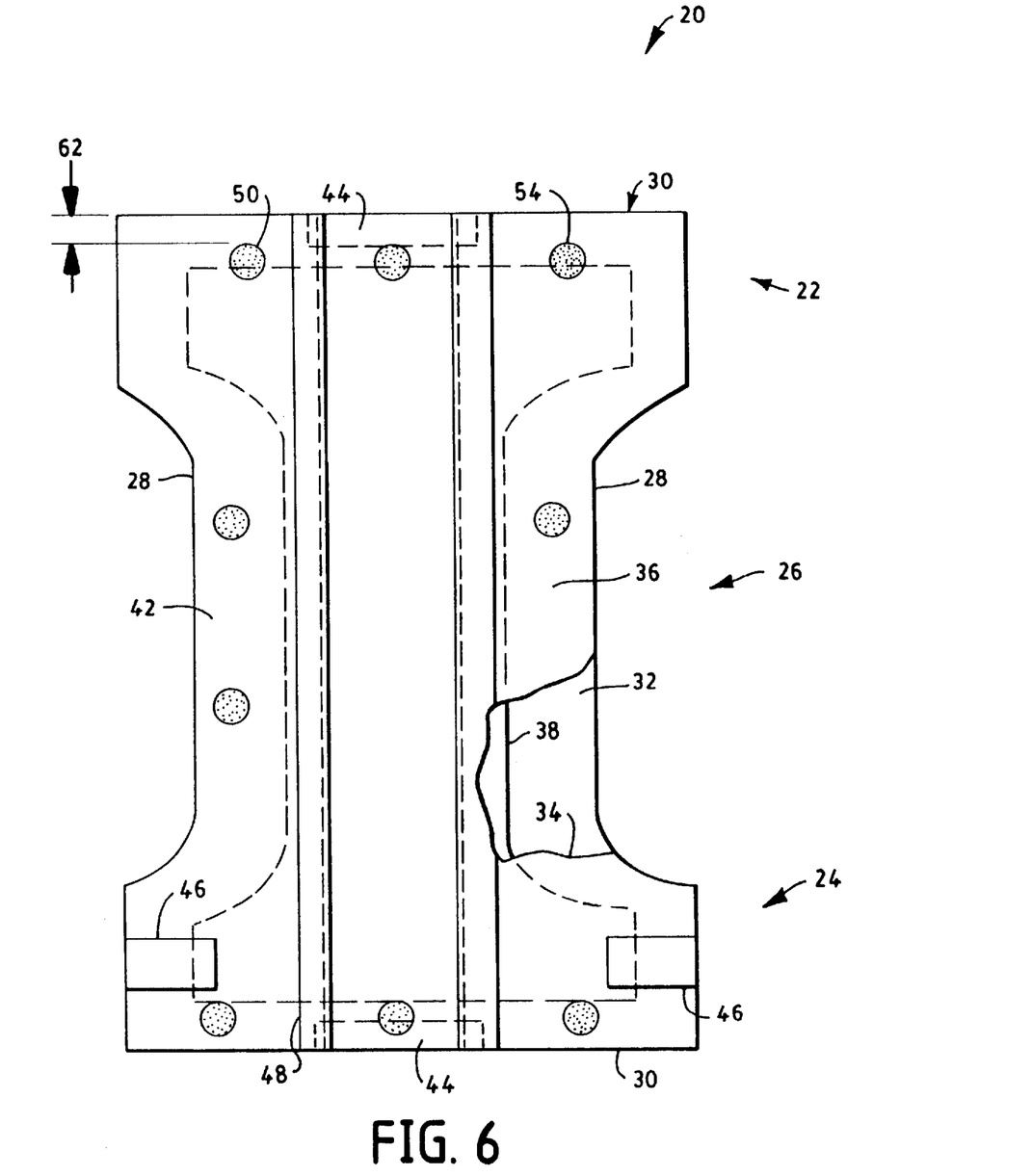
FIG. 6 representatively illustrates a top plan view of yet another example of a disposable diaper according to the present invention.

In a particular aspect of the present invention wherein the diaper 20 includes containment flaps 48 as representatively illustrated in FIGS. 4 and 5, it is desirable that the strips of adhesive 56 extend laterally across at least a portion of the width and, even more desirable, across the entire width of the diaper 20 between the containment flaps 48. In such a configuration, the combination of the strips of adhesive 56 and the containment flips 48 effectively provides a seal and barrier to the flow of body exudates.

As representatively illustrated in FIGS. 4 and 5, the diaper 20 may also include a pair of strips of adhesive 64 which extend longitudinally along the side edges 28 of the diaper 20 in at least the crotch portion 26 of the diaper 20 to reduce the leakage of body exudates around the legs of the wearer. The side strips of adhesive 64 may include several segments of varying lengths or one continuous segment of adhesive. Desirably, the side strips of adhesive 64 include a single continuous segment as representatively illustrated in FIGS.

4 and 5. As illustrated, the side strips of adhesive 64 may have a length 66 of from about 5 to about 52 centimeters and desirably from about 7.5 to about 30 centimeters to provide the desired seal and barrier around the legs of the wearer. The strips of adhesive 64 may also have a width 68 of from about 0.2 to about 5 centimeters and desirably from about 0.2 to about 2 centimeters and a thickness 52 of from about 0.001 to about 5 millimeters. The strips of adhesive 64 may also be spaced inwardly a distance 70 of from about 0 to about 4 and desirably from about 0 to about 2 centimeters.

In an alternative configuration, the diaper 20 may include a pattern of dots of adhesive located on the bodyfacing surface 36 of the bodyside liner 34 of the diaper 20. The dots of adhesive are configured to additionally support and maintain the diaper 20 in proper position on the wearer and selectively provide a seal or barrier to reduce leakage of body exudates. For example, as representatively illustrated in FIG. 6, the diaper 20 may include a pattern of dots 54 of adhesive which are located on the bodyside liner 34 along the outer periphery of the diaper 20. Desirably, the dots 64 of adhesive are located on the bodyfacing surface 36 of the bodyside liner 34 at least along the longitudinal end edges 30 of the diaper 20 to reduce leakage of body exudates along the waist of the wearer. The dots 64 of adhesive may also be located along the side edges 28 of the diaper 20 in at least the crotch portion 26 to reduce the leakage of body exudates around the legs of the wearer.

If it is also desirable that the adhesive 50 of the different aspects of the present invention function as a seal or barrier or maintain the diaper 20 in contact with the wearer during use, the adhesive 50 should have a total adhesive surface area of at least about 10 and desirably from about 10 to about 383 square centimeters. Moreover, if it is desirable that the adhesive 50 function as a dam or barrier to the flow of exudates, the adhesive 50 should have a thickness 52 of at least about 1 millimeters and desirably from about 1 to about 5 millimeters.

Even though the adhesive 50 of the present invention desirably has a low level of adhesion to the wearer, the adhesive may still function to provide the other benefits described above due to forces applied by the wearer which may tend to cause the adhesive to remain adhered or readhered to the skin of the wearer during use. The adhesive 50 of the present invention can be applied to the bodyfacing surface 36 of the bodyside liner 34 by methods known to those skilled in the art. For example, the adhesive 50 may be applied by slot coating, screen printing, or extrusion techniques as are known.

The diaper 20 according to the different aspects of the present invention may further include at least one removable cover sheet which is used to cover the adhesive 50 prior to the time when the diaper is to be fastened to the wearer's body. The removable cover sheet serves to protect the adhesive 50 from securing to other surfaces prior to use and to prevent contamination of the adhesive 50. Suitable materials for the removable cover sheet include materials which are capable of being releasably secured to the adhesive 50.

EXAMPLES

The following examples are presented to provide a more detailed understanding of the Invention. The particular materials and parameters are exemplary and are not intended to limit the scope of the invention.
Test Methods
Rheological Properties The rheological analysis of an adhesive sample is a method of determining the viscoelastic properties of the adhesive sample. The rheological measurements are obtained by using a Rheometrics Dynamic Spectrometer, model RDS IIE, available from Rheometrics Inc., Piscataway, N.J., by using the procedures well known to those skilled in the art and recommended in the operating manual, the contents of which are herein incorporated by reference. The Theological properties are measured for adhesive samples having a thickness of between about 1 to about 4 millimeters. The adhesive sample is cut into a 25 millimeter diameter circle and placed between two, 25 millimeter diameter parallel plate fixtures of the spectrometer. The upper plate is lowered onto the adhesive sample until a normal force meter indicates a slight deflection. The shear strain applied to the adhesive sample is about 1 percent. The shear storage modulus and the shear loss modulus values for the adhesive sample are measured at a temperature of about 20° C. and at a frequency of about 10 radians per second.
Peel Strength Test This test procedure determines the average load, measured in grams force per unit width of the adhesive pattern, required to remove an adhesive from a surface such as the skin of a wearer in a peel mode. The peel strength of an adhesive sample is determined using a modified Pressure Sensitive Tape Council 180° peel resistance test (PSTC-1) described below. PSTC-1 is a standardized test procedure that is described in greater detail on page 23 of the tenth edition of *Test Methods* copyright 1992, available from Pressure Sensitive Tape Council, 401 North Michigan Avenue, Chicago, Ill., the disclosure of which is herein incorporated by reference. The peel strength values are determined according to the following procedure.
Equipment
1. Tensile tester capable of obtaining a peak load and equipped with an appropriate load cell. A suitable tensile testing system is a Model
2. Materials Test System Sintech Tensile Tester, commercially available from MTS Sintech, Research Triangle Park, N.C. Rubber covered roller, 4.5 pounds, commercially available from Chemsultants International Network, Mentor, Ohio, under the part number RD-1000.
3. Stainless steel plate having dimensions 5.1 centimeters ×15.24 centimeters and a thickness of 0.152 centimeters.
4. Double sided adhesive tape, 2.54 centimeters wide, 3M #665 commercially available from the 3M Corporation, Minneapolis, Minn.
Sample Preparation
1. A piece of the double sided adhesive tape is attached to the top and bottom edges of the stainless steel plate.
2. A piece of embossed polyethylene film having a thickness of 2 mils, dimensions of 5.1×15.24 centimeters, and a regular taffeta pattern which is commercially available from Edison Plastics Company is secured to the adhesive tape. The female side of the film is attached to the tape.
3. An adhesive test sample is molded and cured on a flexible substrate such as a non-woven material or polyethylene film in a predetermined pattern. Alternatively, if the adhesive has been previously molded and cured on the bodyside liner of an absorbent article, the portion of the bodyside liner containing the adhesive may be removed and used in the test.
4. The width of the adhesive pattern is measured and recorded.
5. A leading strip of non-stretchable material, such as conventional release paper, is attached to an end of the flexible substrate.
6. The adhesive test sample is placed on the male side of the polyethylene film and pressed down with the roller, one pass in each direction at approximately 300 millimeters per minute.

Test Procedure
1. After the sample is prepared, the sample is immediately inserted into the tensile tester.
2. The jaws of the tester are initially set 17.78 centimeters apart.
3. One end (1.27 cm) of the steel plate is centered and secured in the stationary jaw and the leading strip is doubled back and clamped in a centered arrangement in the moving jaw of the tester.
4. The tester is programmed to travel at a rate of 300 millimeters per minute.
5. The crosshead is started in motion.
6. The average load is recorded and the peel strength of the sample is determined by dividing the average load by the width of the adhesive pattern.

Shear Strength Test

This test procedure determines the peak load, measured in grams force per unit area, required to remove and adhesive from a surface such as the skin of a wearer in a shear mode.

Eguipment
1. Tensile tester capable of obtaining a peak load and equipped with an appropriate load cell. A suitable tensile testing system is a Model 2 Materials Test System Sintech Tensile Tester, commercially available from MTS Sintech, Research Triangle Park, N.C.
2. Rubber covered roller, 4.5 pounds, commercially available from Chemsultants International Network, Mentor, Ohio, under the part number RD-1000.
3. Stainless steel plate having dimensions 5.1 centimeters ×15.24 centimeters and a thickness of 0.15 centimeters.
4. Double sided adhesive tape, 2.54 centimeters wide, 3M #665 commercially available from the 3M Corporation, Minneapolis, Minn.

Sample Preparation
1. A piece of the double sided adhesive tape is attached to the top and bottom edges of the stainless steel plate.
2. A piece of embossed polyethylene film having a thickness of 2 mils, dimensions of 5.1×15.24 centimeters, and a regular taffeta pattern which is commercially available from Edison Plastics Company is secured to the adhesive tape. The female side of the film is attached to the tape.
3. An adhesive test sample is molded and cured on a flexible substrate such as a non-woven material or polyethylene film in a predetermined pattern. Alternatively, if the adhesive has been previously molded and cured on the bodyside liner of an absorbent article, the portion of the bodyside liner containing the adhesive may be removed and used in the test.
4. The area of the adhesive pattern is measured and recorded.
5. A leading strip of non-stretchable material, such as conventional release paper, is attached to an end of the flexible substrate.
6. The adhesive test sample is placed on the male side of the polyethylene film and pressed down with the roller, one pass in each direction at approximately 300 millimeters per minute.

Test Procedure
1. After the sample is prepared, the sample is inserted into the tensile tester.
2. The jaws of the tester are initially set 15.24 centimeters apart.
3. One edge (1.27 cm) of the steel plate is centered and secured in the stationary jaw and the leading strip is doubled back and clamped in a centered arrangement in the moving jaw of the tester.
4. The tester is programmed to travel at a rate of 100 millimeters per minute.
5. The crosshead is started in motion.
6. The peak load is recorded. The shear strength is determined by dividing the peak load by the area of the adhesive pattern. The shear strength is determined immediately after the sample is prepared to determine an "initial shear strength" of the adhesive or after waiting for a period of 30 minutes after the sample is prepared to determine an "aged shear strength."

Cycle Test

This test procedure determines the adhesion level between an adhesive and a substrate as it is subjected to a cyclical loading. The test measures the number of cycles required to achieve a peak load of 30 grams per square centimeter between the adhesive and the substrate. The test is indicative of how the adhesive will function when adhered to an active wearer.

Equipment
1. Tensile tester capable of obtaining a peak load and equipped with an appropriate load cell. A suitable tensile testing system is a Model 810 Materials Test System, commercially available from MTS Sintech, Research Triangle Park, N.C.
2. Rubber covered roller, 4.5 pounds, commercially available from Chemsultants International Network, Mentor, Ohio, under the part number RD-1000.
3. Stainless steel plate having dimensions of 5.1 centimeters ×15.24 centimeters and a thickness of 0.15 centimeters.
4. Double sided adhesive tape, 2.54 centimeters wide, 3M #665 commercially available from the 3M Corporation, Minneapolis, Minn.

Sample Preparation
1. A piece of the double sided adhesive tape is attached to the top and bottom edges of the stainless steel plate.
2. A piece of embossed polyethylene film having a thickness of 2 mils, dimensions of 5.1×15.24 centimeters, and a regular taffeta pattern which is commercially available from Edison Plastics Company is secured to the adhesive tape. The female side of the film is attached to the tape.
3. An adhesive test sample is molded and cured on a flexible substrate such as a non-woven material or polyethylene film. Alternatively, if the adhesive has been previously molded and cured on the bodyside liner of an absorbent article, the portion of the bodyside liner containing the adhesive may be removed and used in the test.
4. A leading strip of non-stretchable material, such as conventional release paper, is attached to an end of the flexible substrate.
5. The adhesive test sample is placed on the male side of the polyethylene film and pressed down with the roller, one pass in each direction at approximately 300 millimeters per minute.

Test Procedure
1. After the sample is prepared, the sample is inserted into the tensile tester.
2. The jaws of the tester are initially set 15.24 centimeters apart.
3. One edge (1.27 cm) of the steel plate is centered and secured in the stationary jaw and the leading strip is doubled back and clamped in a centered arrangement in the moving jaw of the tester.
4. The tester is programmed to cycle at a frequency of 1 Hz at an amplitude of about 3.8 centimeters.
5. The tester is started.
6. The maximum load is recorded for each cycle. The number of cycles that have lapsed when the load reaches a value which is at or below 30 grams per square centimeter is recorded as the cyclic shear value.

Example 1

An adhesive which is available from Findley Adhesives Company under the trade designation "Findley 2465-Y" was slot coated on a polypropylene spunbond nonwoven material having a basis weight of 0.8 ounces per square yard to provide three samples. The adhesive on each sample had a width of 6.35 millimeters and a length of 25.4 millimeters. The samples were then subjected to the Peel Strength Test, Shear Strength Test, and Cyclic Test.

The samples had an average peel strength of 95 grams per 12.5 millimeters width, an average initial shear strength of 847 grams per 1.61 square centimeters, an average aged shear strength of 716 grams per 1.61 square centimeters, and a cyclic shear value of 45 cycles. The data is also recorded in Table 1. This data corresponds to an average peel strength of 76 grams per centimeter of width, an average initial shear strength of 526 grams per square centimeter, and an average aged shear strength of 445 grams per square centimeter.

Example 2

An adhesive which is available from Findley Adhesives Company under the trade designation "Findley 2465-E8" was slot coated on a polypropylene spunbond nonwoven material having a basis weight of 0.8 ounces per square yard to provide three samples. The adhesive on each sample had a width of 6.35 millimeters and a length of 25.4 millimeters. The samples were then subjected to the Peel Strength Test, Shear Strength Test, and Cyclic Test.

The samples had an average peel strength of 50 grams per 12.5 millimeters width, an average initial shear strength of 268 grams per 1.61 square centimeters, an average aged shear strength of 134 grams per 1.61 square centimeters, and a cyclic shear value of 1 cycle. The data is also recorded in Table 1. This data corresponds to an average peel strength of 40 grams per centimeter of width, an average initial shear strength of 166 grams per square centimeter, and an average aged shear strength of 83 grams per square centimeter.

Example 3

An adhesive whose components were commercially available from Dow Corning Company, Midland, Mich., under the trade designation Q3-6636 Part A and Q3-6636 Part B was prepared as follows. The Part A and Part B components were mixed in the proportion 5.6/4.6 by weight to provide the adhesive. A first mold was prepared by cutting a 4 inch by 4 inch square through a Teflon-coated sheet having a length of about 5 inches, a width of about 5 inches and a thickness of about 0.062 inches. The mold was supported by another Teflon-coated sheet having the same length, width and thickness dimensions. The adhesive was poured into the mold cavity to the top of the Teflon-coated sheet, for a thickness of about 0.062 inches. The mold assembly was then placed in an air-circulating oven at about 123 degrees centigrade for about 30 minutes and then allowed to cool to ambient temperature. The resulting adhesive had a Shear Storage Modulus of $2.81 \times 10^4$ dynes per square centimeter and a tan delta of 0.353 as measured at about 20° C. and at a frequency of about 10 radians per second.

A second mold was prepared by cutting a slot having a width of 6.35 millimeters and a length of 25.4 millimeters through a Teflon-coated sheet having a thickness of about 0.062 inches. The mold was supported by a laminate of a polypropylene spunbond nonwoven material having a basis weight of 0.8 ounces per square yard and another Teflon-coated sheet. The adhesive was poured into the mold cavity on the polypropylene material to the top of the Teflon-coated sheet, for a thickness of about 0.062 inches. The mold assembly was then placed in an air-circulating oven at about 123 degrees centigrade for about 30 minutes and then allowed to cool to ambient temperature. Three samples of the adhesive were prepared. The samples were then subjected to the Peel Strength Test, Shear Strength Test, and Cyclic Test.

The samples had an average peel strength of 1.0 grams per 12.5 millimeters width, an average initial shear strength of 67 grams per 1.61 square centimeters, an average aged shear strength of 53 grams per 1.61 square centimeters, and a cyclic shear value of 1 cycle. The data is also recorded in Table 1. This data corresponds to an average peel strength of 0.80 grams per centimeter of width, an average initial shear strength of 41.6 grams per square centimeter, and an average aged shear strength of 32.9 grams per square centimeter.

Example 4

An adhesive whose components were commercially available from Dow Corning Company, Midland, Mich., under the trade designation Q3-6636 Part A and Q3-6636 Part B was prepared as follows. The Part A and Part B components were mixed in the proportion 5/5 by weight to provide the adhesive. A first mold was prepared by cutting a 4 inch by 4 inch square through a Teflon-coated sheet having a length of about 5 inches, a width of about 5 inches and a thickness of about 0.062 inches. The mold was supported by another Teflon-coated sheet having the same length, width and thickness dimensions. The adhesive was poured into the mold cavity to the top of the Teflon-coated sheet, for a thickness of about 0.062 inches. The mold assembly was then placed in an air-circulating oven at about 123 degrees centigrade for about 30 minutes and then allowed to cool to ambient temperature. The resulting adhesive had a Shear Storage Modulus of $7.83 \times 10^3$ dynes per square centimeter and a tan delta of 0.984 as measured at about 20° C. and at a frequency of about 10 radians per second.

A second mold was prepared by cutting a slot having a width of 6.35 millimeters and a length of 25.4 millimeters through a Teflon-coated sheet having a thickness of about 0.062 inches. The mold was supported by a laminate of a polypropylene spunbond nonwoven material having a basis weight of 0.8 ounces per square yard and another Teflon-coated sheet. The adhesive was poured into the mold cavity on the polypropylene material to the top of the Teflon-coated sheet, for a thickness of about 0.062 inches. The mold assembly was then placed in an air-circulating oven at about 123 degrees centigrade for about 30 minutes and then allowed to cool to ambient temperature. Three samples of the adhesive were prepared. The samples were then subjected to the Peel Strength Test, Shear Strength Test, and Cyclic Test.

The samples had an average peel strength of 55 grams per 12.5 millimeters width, an average initial shear strength of 142 grams per 1.61 square centimeters, an average aged shear strength of 72 grams per 1.61 square centimeters, and a cyclic shear value of 16 cycles. The data is also recorded in Table 1. This data corresponds to an average peel strength of 44 grams per centimeter of width, an average initial shear strength of 88.2 grams per square centimeter, and an average aged shear strength of 44.7 grams per square centimeter.

Example 5

An adhesive which is available from The National Starch and Chemical Company under the trade designation "8111-

69-2" was screen printed on a polypropylene spunbond nonwoven material having a basis weight of 0.8 ounces per square yard to provide three samples. The adhesive on each sample had a width of 6.35 millimeters and a length of 25.4 millimeters. The adhesive had a Shear Storage Modulus of $5.85 \times 10^5$ dynes per square centimeter and a tan delta of 0.437 as measured at about 20° C. and at a frequency of about 10 radians per second. The samples were then subjected to the Peel Strength Test, Shear Strength Test, and Cyclic Test.

The samples had an average peel strength of 160 grams per 12.5 millimeters width, an average initial shear strength of 834 grams per 1.61 square centimeters, an average aged shear strength of 624 grams per 1.61 square centimeters, and a cyclic shear value of 3 cycles. The data is also recorded in Table 1. This data corresponds to an average peel strength of 128 grams per centimeter of width, an average initial shear strength of 518 grams per square centimeter, and an average aged shear strength of 388 grams per square centimeter.

Example 6

An adhesive which is commercially available from The National Starch and Chemical Company under the trade designation "34-5607" was slot coated on a polypropylene spunbond nonwoven material having a basis weight of 0.8 ounces per square yard to provide three samples. The adhesive on each sample had a width of 6.35 millimeters and a length of 25.4 millimeters. The adhesive had a Shear Storage Modulus of $6.58 \times 10^4$ dynes per square centimeter and a tan delta of 0.274 as measured at about 20° C. and at a frequency of about 10 radians per second. The samples were then subjected to the Peel Strength Test, Shear Strength Test, and Cyclic Test.

The samples had an average peel strength of 170 grams per 12.5 millimeters width, an average initial shear strength of 695 grams per 1.61 square centimeters, and a cyclic shear value of 5 cycles. The data is also recorded in Table 1. This data corresponds to an average peel strength of 136 grams per centimeter of width and an average initial shear strength of 432 grams per square centimeter.

Example 7

An adhesive which is available from The National Starch and Chemical Company under the trade designation "07659-41-3" was screen printed on a polypropylene spunbond nonwoven material having a basis weight of 0.8 ounces per square yard in an adhesive pattern of densified ovals which covered 37 percent of the area in the pattern to provide three samples. The adhesive pattern on each sample had a width of 6.35 millimeters and a length of 25.4 millimeters. The adhesive had a Shear Storage Modulus of $5.83 \times 10^5$ dynes per square centimeter and a tan delta of 0.475 as measured at about 20° C. and at a frequency of about 10 radians per second. The samples were then subjected to the Peel Strength Test. The samples had an average peel strength of 220 grams per 12.5 millimeters width. The data is also recorded in Table 1. This data corresponds to an average peel strength of 176 grams per centimeter of width.

Example 8

An adhesive which was based on polyisobutylene and was formulated from three components was tested. Two components are commercially available from Exxon Chemical Company, a business having offices located in Baytown, Texas, under the trade designation Vistanex L-120 and Butyl 065. The third component is commercially available from Amoco Chemical Company, a business having offices located in Chicago, Ill., under the trade designation Polybutene H-25. About 99.5 parts by weight of L-120, 30 parts by weight Butyl 065 and 89.5 parts by weight Polybutene H-25 were used in the formulation. The components were mixed in a high shear mixer of the type D-51-T which is commercially available from Brabender Industries, a business having offices located in Hackensack, N.J. The mixer was preheated to 70 degrees centigrade. The L-120 and Butyl 065 components were masticated for about five minutes and the temperature of the mixer was raised to 150 degrees centigrade. The Polybutene H-25 was then introduced in small doses over a period of 30 minutes. The formulation was mixed for about five more minutes and then allowed to cool to ambient temperature.

Small portions of the adhesive were then placed between silicone coated release paper and hot pressed at a temperature of about 150 degrees centigrade and five pounds per square inch in a press commercially available from Dake Corporation, a business having offices located in Grand Haven, Michigan. The resulting adhesive film was then laminated to a spunbond polypropylene nonwoven material having a basis weight of about 0.8 ounces per square yard in the Dake press at a temperature of about 100 degrees centigrade and a pressure of about 10 psi. The adhesive had a Shear Storage Modulus of. $9.37 \times 10^5$ dynes per square centimeter and a tan delta of 0.136 as measured at about 20° C. and at a frequency of about 10 radians per second. The samples were then subjected to the Peel Strength Test, Shear Strength Test, and Cyclic Test.

The samples had an average peel strength of 75 grams per 12.5 millimeters width, an average initial shear strength of 460 grams per 1.61 square centimeters, an average aged shear strength of 388 grams per 1.61 square centimeters, and a cyclic shear value of 1 cycle. The data is also recorded in Table 1. This data corresponds to an average peel strength of 60 grams per centimeter of width, an average initial shear strength of 286 grams per square centimeter, and an average aged shear strength of 241 grams per square centimeter.

Comparative Example 1

An adhesive which is commercially available from Findley Adhesives Company under the trade designation "Findley H2292" was screen printed on a polypropylene spunbond nonwoven material having a basis weight of 0.8 ounces per square yard in an adhesive pattern of densified ovals which covered 37 percent of the area in the pattern to provide three samples. The adhesive was being used as a construction adhesive on Huggies® Supreme diapers which were commercially available from Kimberly-Clark. The adhesive pattern on each sample had a width of 6.35 millimeters and a length of 25.4 millimeters. The adhesive had a Shear Storage Modulus of $9.04 \times 10^5$ and a tan delta of 1.509 as measured at about 20° C. and at a frequency of about 10 radians per second. The samples were then subjected to the Peel Strength Test and Shear Strength Test.

The samples had an average peel strength of 450 grams per 12.5 millimeters width and an average initial shear strength of 1045 grams per 1.61 square centimeters. The data is also recorded in Table 1. This data corresponds to an average peel strength of 360 grams per centimeter of width and an average initial shear strength of 650 grams per square centimeter. The peel strength and shear strength of this adhesive were very high and consequently the adhesive had a very high adhesion to the polyethylene and would be too aggressive for the different aspects of the present invention.

Comparative Example 2

An adhesive which is available from The National Starch and Chemical Company under the trade designation "7659-41-3" was screen printed on a polypropylene spunbond nonwoven material having a basis weight of 0.8 ounces per square yard to provide three samples. The adhesive on each sample had a width of 6.35 millimeters and a length of 25.4 millimeters. The adhesive had a Shear Storage Modulus of $5.83 \times 10^5$ dynes per square centimeter and a tan delta of 0.475 as measured at about 20° C. and at a frequency of about 10 radians per second. The samples were then subjected to the Peel Strength Test, Shear Strength Test, and Cyclic Test.

The samples had an average peel strength of 380 grams per 12.5 millimeters width, an average initial shear strength of 1321 grams per 1.61 square centimeters, an average aged shear strength of 1103 grams per 1.61 square centimeters, and a cyclic shear value of 22 cycles. The data is also recorded in Table 1. This data corresponds to an average peel strength of 304 grams per centimeter of width, an average Initial shear strength of 820 grams per square centimeter, and an average aged shear strength of 685 grams per square centimeter. The peel strength and shear strength of this adhesive were very high and consequently the adhesive had a very high adhesion to the polyethylene and would be too aggressive for the different aspects of the present invention.

Comparative Example 3

An adhesive whose components were commercially available from Dow Corning Company, Midland, Mich., under the trade designation Q3-6636 Part A and Q3-6636 Part B was prepared as follows. The Part A and Part B components were mixed in the proportion 3.5/6.5 by weight to provide the adhesive. A mold was prepared by cutting a slot having a width of 6.35 millimeters and a length of 25.4 millimeters through a Teflon-coated sheet having a thickness of about 0.062 inches. The mold was supported by a laminate of a polypropylene spunbond nonwoven material having a basis weight of 0.8 ounces per square yard and another Teflon-coated sheet. The adhesive was poured into the mold cavity on the polypropylene material to the top of the Teflon-coated sheet, for a thickness of about 0.062 inches. The mold assembly was then placed in an air-circulating oven at about 123 degrees centigrade for about 30 minutes and then allowed to cool to ambient temperature. Three samples of the adhesive were prepared. The samples were then subjected to the Peel Strength Test, Shear Strength Test, and Cyclic Test.

The samples fell off the tester before it could be started in motion in the Peel Strength Test and had an average initial shear strength of 54 grams per 1.61 square centimeters. The data is also recorded in Table 1. This data corresponds to an average initial shear strength of 33.5 grams per square centimeter. As a result, this adhesive would not provide even a temporary securement to a wearer to facilitate the fastening of the article about the wearer as desired in the present invention.

TABLE 1

| | Shear Storage Modulus (dynes/cm$^2$) | Tan Delta | Peel Strength (grams/ 12.5 mm) | Initial Shear Strength (grams/ 1.61 cm$^2$) | Aged Shear Strength (grams/ 1.61 cm$^2$) | Cyclic Shear (cycles) |
|---|---|---|---|---|---|---|
| Ex. 1 | | | 95 | 847 | 716 | 45 |
| Ex. 2 | | | 50 | 268 | 134 | 1 |
| Ex. 3 | 2.81 × 10$^4$ | 0.353 | 1 | 67 | 53 | 1 |
| Ex. 4 | 7.83 × 10$^3$ | 0.984 | 55 | 142 | 72 | 16 |
| Ex. 5 | 5.85 × 10$^5$ | 0.437 | 160 | 834 | 624 | 3 |
| Ex. 6 | 6.58 × 10$^4$ | 0.274 | 170 | 695 | | 5 |
| Ex. 7 | 5.83 × 10$^5$ | 0.475 | 220 | | | |
| Ex. 8 | 9.37 × 10$^5$ | 0.136 | 75 | 460 | 388 | 1 |
| C. Ex. 1 | 9.04 × 10$^5$ | 1.509 | 450 | 1045 | | |
| C. Ex. 2 | 5.83 × 10$^5$ | 0.475 | 380 | 1321 | 1103 | 22 |
| C. Ex. 3 | | | * | 54 | | |

*Fell off before test could be run

The results from the examples representatively show the effect of the different variables such as, the rheological properties of the adhesive and the pattern of the adhesive, on the ability of the adhesive to provide sufficient adhesion to a surface without being too aggressive or becoming permanently adhered. For example, the data shows that: as the shear storage modulus increases, the ability of the adhesive to release increases; and as the percent area covered by the adhesive pattern increases, the adhesion level of the adhesive increases.

The adhesives in the examples are representative of those that can be used in the different aspects of the present invention to provide the desired temporary securement of the absorbent article to the body of the wearer without causing irritation or red marking. Whereas, the adhesives in the comparative examples are representative of those that are either too aggressive or not aggressive enough for the present invention.

Accordingly, the present invention advantageously provides an absorbent article which has improved fastenability, fit and performance. In one aspect, the present invention includes the use of an adhesive on the bodyfacing surface of an absorbent article to improve the fastening ergonomics to allow the care-giver to properly position and fasten the absorbent article about the waist of a wearer on the first try. The use of an adhesive to at least temporarily secure the front portion of the article to the wearer during attachment allows the care-giver to use both hands simultaneously to fasten the article about the wearer. As such, the present invention can provide an absorbent article which has reduced leakage because it is easier to position the article on the wearer to obtain the optimum fit.

Moreover, in another aspect, the present invention advantageously provides an absorbent article which has adhesive on it's bodyfacing surface at the leg and waist opening regions to provide a seal to further reduce the leakage of bodily exudates. In still another aspect, the present invention provides an absorbent article which has adhesive on it's bodyfacing surface in the waist regions of the article to reduce the tendency of the end edges of the article to rollover or droop and sag. Accordingly, the present invention provides an absorbent article which is easier to fasten about the wearer and has an improved fit, reduced leakage and increased consumer acceptance.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. An absorbent article which includes a bodyfacing surface, a front portion, a rear portion, a crotch portion which extends between and connects said front portion to said rear portion, a pair of side edges and a pair of longitudinal end edges, said absorbent article comprising:
   a) an outer cover,
   b) a bodyside liner which is superposed on said outer cover;
   c) an absorbent core which is located between said outer cover and said bodyside liner; and
   d) an adhesive which is located on said bodyfacing surface of said absorbent article wherein said adhesive is configured to provide a peel strength of no more than about 300 grams per centimeter of width and wherein said adhesive is configured to contact a wearer's body during use to at least temporarily secure said bodyfacing surface of said absorbent article directly to said wearer's body.

2. The absorbent article according to claim 1 wherein said adhesive is configured to provide a peel strength of no more than about 240 grams per centimeter of width.

3. The absorbent article according to claim 1 wherein said adhesive defines a shear storage modulus of from about $1.0 \times 10^3$ to about $6.0 \times 10^6$ dynes per square centimeter as measured at a temperature of about 20° C. and at a frequency of about 10 radians per second.

4. The absorbent article according to claim 1 wherein said adhesive defines a shear storage modulus of from about $4.0 \times 10^4$ to about $6.0 \times 10^6$ dynes per square centimeter as measured at a temperature of about 20° C. and at a frequency of about 10 radians per second.

5. The absorbent article according to claim 1 wherein said adhesive is configured to provide an initial shear strength of no more than about 600 grams per square centimeter.

6. The absorbent article according to claim 1 wherein said adhesive is configured to provide an initial shear strength of from about 0 to about 530 grams per square centimeter.

7. The absorbent article according to claim 1 wherein said adhesive is configured to provide an aged shear strength of no more than about 500 grams per square centimeter.

8. The absorbent article according to claim 1 wherein said adhesive is configured to provide a cyclic shear value of no more than about 100 cycles.

9. The absorbent article according to claim 1 wherein said adhesive is configured to provide a cyclic shear value of from about 0 to about 50 cycles.

10. The absorbent article according to claim 1 wherein said adhesive is located on said bodyside liner in a center portion adjacent at least a portion of one of said longitudinal end edges of said absorbent article wherein said adhesive is configured to contact said wearer's body in use.

11. The absorbent article according to claim 1 wherein said adhesive is located on said bodyside liner adjacent at least a portion of both of said longitudinal end edges of said absorbent article.

12. The absorbent article according to claim 1 wherein said adhesive is located on said bodyside liner adjacent at least a portion of both of said side edges of said absorbent article.

13. The absorbent article according to claim 1 wherein said bodyfacing surface of said bodyside liner defines a surface area and said adhesive is located on less than about 25 percent of said surface area.

14. The absorbent article according to claim 1 wherein said adhesive defines an adhesive area which is from about 0.1 to about 10 square centimeters.

15. The absorbent article according to claim 1 wherein said adhesive is arranged in a pattern of dots and wherein each of said dots defines an area of from about 0.04 to about 9 square centimeters.

16. The absorbent article according to claim 1 wherein said adhesive defines a thickness of from about 0.001 to about 1 millimeter.

17. The absorbent article according to claim 1 and further comprising a pair of longitudinally extending containment flaps located along said side edges of said absorbent article wherein said adhesive includes a strip of adhesive which extends laterally between said containment flaps.

18. The absorbent article according to claim 1 and further comprising a pair of fasteners located along the side edges of said absorbent article which are configured to maintain said article about a waist of said wearer in use.

19. An absorbent article which includes a front portion, a rear portion, a crotch portion which extends between and connects said front portion to said rear portion, a pair or side edges and a pair of longitudinal end edges, said absorbent article comprising:
   a) an outer cover;
   b) a bodyside liner which is superposed on said outer cover and which includes a bodyfacing surface;
   c) an absorbent core which is located between said outer cover and said bodyside liner; and
   d) an adhesive which is located on said bodyfacing surface of said bodyside liner and which is configured to contact a wearer's body during use to at least temporarily secure said bodyfacing surface of said bodyside liner of said absorbent article directly to said wearer's body wherein said adhesive is configured to provide a peel strength of no more than about 300 grams per centimeter of width, an aged shear strength of no more than about 500 grams per square centimeter, and a cyclic shear value of no more than about 50 cycles.

20. The absorbent article according to claim 19 wherein said adhesive is located on said bodyfacing surface of said bodyside liner in said front portion of said absorbent article and wherein said adhesive is configured to at least temporarily secure said front portion of said absorbent article to said wearer's body to assist in positioning and fastening said absorbent article about said wearer's body.

21. A diaper which includes a front portion, a rear portion, a crotch portion which extends between and connects said front portion to said rear portion, a pair of side edges and a pair of longitudinal end edges, said diaper comprising:
   a) an outer cover;
   b) a bodyside liner which is superposed on said outer cover and which includes a bodyfacing surface;
   c) an absorbent core which is located between said outer cover and said bodyside liner; and
   d) an adhesive which is located on said bodyfacing surface of said bodyside liner adjacent at least a portion of said longitudinal end edge of said diaper in said front portion of said diaper and which is configured to contact a wearer's body during use to at least temporarily secure said bodyfacing surface of said bodyside liner in said front portion of said diaper directly to said wearer's body to assist in positioning and fastening said diaper about said wearer's body.

22. The diaper according to claim 21 wherein said adhesive includes a strip of adhesive which extends laterally along a center portion of said longitudinal end edge of said diaper for a length of from about 1 to about 35 centimeters wherein said strip of adhesive is configured to contact said wearer's body in use.

23. The diaper according to claim 22 wherein said strip of adhesive defines a width of from about 0.5 to about 5 centimeters.

24. The diaper according to claim 21 wherein said adhesive is located on said bodyside liner in a pattern of dots and wherein each of said dots defines an area of from about 0.04 to about 9 square centimeters.

25. The diaper according to claim 21 wherein said adhesive defines an adhesive area which is from about 0.1 to about 10 square centimeters.

26. The diaper according to claim 21 wherein said adhesive defines a shear storage modulus of at least about $1.0 \times 10^3$ dynes per square centimeter as measured at a temperature of about 20° C. and at a frequency of about 10 radians per second.

27. The diaper according to claim 21 wherein said adhesive is configured to provide a peel strength of no more than about 300 grams per centimeter of width and an initial shear strength of no more than about 600 grams per square centimeter.

28. The diaper according to claim 21 wherein said adhesive is configured to provide an aged shear strength of no more than about 500 grams per square centimeter.

29. The diaper according to claim 21 wherein said adhesive is configured to provide a cyclic shear value of no more than 100 cycles.

30. The diaper according to claim 21 and further comprising a pair of longitudinally extending containment flaps located along said side edges of said diaper wherein said adhesive includes a strip of adhesive which extends laterally between said containment flaps.

31. The diaper according to claim 21 and further comprising a pair of fasteners located along said side edges of said diaper which are configured to maintain said diaper about a waist of said wearer in use.

* * * * *